(12) United States Patent
Olszewski et al.

(10) Patent No.: US 9,031,632 B2
(45) Date of Patent: May 12, 2015

(54) IMAGING BASED VIRUS DETECTION

(75) Inventors: Mark E. Olszewski, Solon, OH (US); Matthew J. Walker, Willoughby, OH (US)

(73) Assignee: Koninklijke Philips N.V., Eindhoven (NL)

( * ) Notice: Subject to any disclaimer, the term of this patent is extended or adjusted under 35 U.S.C. 154(b) by 479 days.

(21) Appl. No.: 13/503,997

(22) PCT Filed: Oct. 29, 2010

(86) PCT No.: PCT/IB2010/054910
§ 371 (c)(1),
(2), (4) Date: Apr. 25, 2012

(87) PCT Pub. No.: WO2011/061652
PCT Pub. Date: May 26, 2011

(65) Prior Publication Data
US 2012/0209093 A1    Aug. 16, 2012

Related U.S. Application Data (60) Provisional application No. 61/263,063, filed on Nov. 20, 2009.

(51) Int. Cl.
*A61B 6/00* (2006.01)
*A61B 6/03* (2006.01)
(Continued)

(52) U.S. Cl.
CPC ............... *A61B 6/5217* (2013.01); *A61B 6/032* (2013.01); *A61B 8/485* (2013.01); *A61B 8/5223* (2013.01); *G06F 19/321* (2013.01); *G06F 19/345* (2013.01); *G06F 19/3493* (2013.01)

(58) Field of Classification Search
CPC ............................... A61B 6/5217; A61B 5/00
USPC ........................................ 600/407, 410, 425
See application file for complete search history.

(56) References Cited

U.S. PATENT DOCUMENTS 6,320,976 B1   11/2001  Murthy et al.
6,574,304 B1    6/2003  Hsieh et al.
(Continued)

FOREIGN PATENT DOCUMENTS

WO    2007144854 A2   12/2007
WO    2011048547 A1    4/2011

OTHER PUBLICATIONS

Abella, H. A.; X-rays and CT offer predictive power for swine flu diagnosis; 2009; Diagnostic Imaging; URL:http://www.diagnosticimaging.com/digital-x-ray/content/article/113619/1425699.
(Continued)

*Primary Examiner* — Peter Luong (57) ABSTRACT

A method for detecting a virus in a patient based on imaging data includes scanning a region of interest of the patient with an imaging device and generating imaging data indicative of the region of interest, identifying at least one marker in the image data that corresponds to the virus based on the identified at least one marker and a set of predetermined imageable markers that correspond to the virus, classifying the virus as a particular strain of the virus based on a set of classification rules, and generating a signal indicative of the particular strain. The method optionally includes generating a signal indicative of the classification and electronically conveying the signal to at least one entity.

24 Claims, 4 Drawing Sheets

(51) Int. Cl.
*G06F 19/00* (2011.01)
*A61B 8/08* (2006.01)

(56) References Cited

U.S. PATENT DOCUMENTS

| | | | |
|---|---|---|---|
| 7,244,230 B2 | 7/2007 | Duggirala et al. | |
| 8,382,668 B2 * | 2/2013 | Harra et al. | 600/365 |
| 2003/0187615 A1 | 10/2003 | Epler et al. | |
| 2004/0101181 A1 | 5/2004 | Giger et al. | |
| 2009/0006131 A1 | 1/2009 | Unger et al. | |

OTHER PUBLICATIONS

Agarwal, P. P., et al.; Chest Radiographic and CT Findings in Novel Swine-Origin Influenza A (H1N1) Virus (S-OIV) Infection; 2009: AJR;193:1-6.

Ajlan, A M., et al.; Swine-Origin Influenza A (H1N1) Viral Infection: Radiographic and CT Findings; 2009; AJR:193:1-6.

Blaffert, T., et al.; Lung lobe modeling and segmentation with individualized surface meshes; 2008; Proc. SPIE; vol. 6914:abstract.

Freedman, M., et al.; Computer-aided detection of Severe Acute Respiratory Syndrome (SARS) on chest radiography; 2004; Computer Assisted Radiology and Surgery; vol. 1268; abstract.

Lee, C. W., et al.; Pulmonary Complication of Novel Influenza A (H1N1) Infection: Imaging Features in Two Patients; 2009; Korean J. Radiol.; 10(6)531-534.

Louie, J. K., et al.; Factors Associated with Death or Hospitalization Due to Pandemic 2009 Influenza A (H1N1) Infection in California; 2009; JAMA; 302(17)1896-1902.

Mollura, D. J., et al.; Imaging Findings in a Fatal Case of Pandemic Swine-Origin Influenza A (H1N1); 2009; AJR; 193:1500-1503.

Spyros, T., et al.; Mining patterns of lung infections in chest radiographs; 2009; http://www.debugit.eu/documents/IFIPAIA12009.pdf.

Wiemker, R., et al.; Automated assessment of bronchial lumen, wall thickness and bronchoarterial diameter ratio of the tracheobronchial tree using high-resolution CT; 2004; Computer Assisted Radiology and Surgery; vol. 1268; abstract.

Wiemker, R., et al.; Aspects of computer-aided detection (CAD) and volumetry of pulmonary nodules using multislice CT; 2005; The British Journal of Radiology; Special Issue; 78:S46-S56.

* cited by examiner

IMAGING BASED VIRUS DETECTION

CROSS REFERENCE TO RELATED APPLICATIONS

This application claims the benefit of U.S. provisional application Ser. No. 61/263,063 filed Nov. 20, 2009, which is incorporated herein by reference.

The following generally relates to imaging based virus detection and is described with particular application to computed tomography (CT). However, it also amenable to other imaging modalities, including x-ray, magnetic resonance imaging (MRI), positron emission tomography (PET), single photon emission computed tomography (SPECT), ultrasound (US), and/or other imaging modalities.

The influenza (flu) H1N1 virus is a swine-origin influenza A (H1N1) subtype responsible for the 2009 flu pandemic. Existing seasonal flu vaccines provide no protection from contracting the swine-origin influenza virus (S-OIV). The literature indicates that influenza A (H1N1) virus is more contagious than seasonal flu and that infected people are contagious for a longer period of time than those infected with seasonal flu, with the S-OIV preferentially affecting certain populations.

The literature has indicated that while most cases are mild and self-limited, S-OIV infection in high-risk patients is more likely to lead to severe illness and even death. Populations at increased risk include children younger than 5 years old, adults 65 years old or older, patients with other chronic ailments (e.g., asthma, diabetes, cardiac disease, renal disease, neurocognitive disease, and neuromuscular disorders), and immunosuppressed patients. In these populations, the time from symptom onset to hospitalization and intensive care may be less than twenty four hours.

Given the possible severity of the disease, its potential pandemic nature, and its associated risks, a timely and accurate detection and diagnosis of S-OIV would be advantageous. Unfortunately, the diagnosis and differentiation of pandemic S-OIV from seasonal flu and other seasonal infectious diseases is currently hampered by the similarity of its signs and symptoms. As such, some cases of S-OIV are treated like seasonal flu or other illness, and in some instances, it is not until the subject is hospitalized that the subject is diagnosed with having contracted the S-OIV.

Three articles, Mollura et al., "Imaging Findings in a Fatal Case of Pandemic Swine-Origin Influenza A (H1N1)," American Journal of Roentgenology, 2009, 193:1-4, Ajlan et al., "Swine-Origin Influenza A (H1N1) Viral Infection: Radiographic and CT Findings," American Journal of Roentgenology, 2009, 193:1-6, and Agarawl et al., "Chest Radiographic and CT Findings in Novel Swine-Origin Influenza A (H1N1) Virus (S-OIV) infection," American Journal of Roentgenology, 2009, 193:1-6, review x-ray radiograph and CT findings in subjects diagnosed with fatal S-OIV infection and in subjects with presumed/laboratory-confirmed S-OIV infection.

Aspects of the present application address the above-referenced matters and others.

According to one aspect, a method for detecting a virus in a patient based on imaging data includes scanning a region of interest of the patient with an imaging device and generating imaging data indicative of the region of interest, identifying at least one marker in the image data that corresponds to the virus based on the identified at least one marker and a set of predetermined imageable markers that correspond to the virus, classifying the virus as a particular strain of the virus based on a set of classification rules, and generating a signal indicative of the particular strain.

In another embodiment, a system includes a virus detection apparatus that detects a virus in a patient based on imaging data. The virus detection apparatus includes a data analyzer that analyzes the image data and identifies at least one feature in the image data that corresponds to the virus based on a set of predetermined features that correspond to the virus. The data analyzer also includes a virus classifier that classifies the virus as a particular strain of the identified virus based on the feature and generates a signal indicative of the particular strain.

In another embodiment, a computer readable storage medium includes instructions which, when executed by a computer, cause the computer to perform various acts such as scanning a region of interest of a patient and generating imaging data indicative of the region of inertest, detecting a presence of a virus infection in the patient based on the imaging data, and classifying the infection as a particular strain of the virus.

The invention may take form in various components and arrangements of components, and in various steps and arrangements of steps. The drawings are only for purposes of illustrating the preferred embodiments and are not to be construed as limiting the invention.

The following describes a system and/or method that facilitates identifying infectious viruses, such as influenza (e.g., S-OIV), in a subject based on a combination of imaging data and at least one of the following: predetermined imageable markers due to the virus, machine learning algorithms, patient information, and/or publically disseminated information related to the virus. By using such data, viruses like S-OIV may be detected and classified early, which may facilitate inhibiting the spread of S-OIV through a population, prioritizing dissemination of vaccines and/or healthcare workers to the public, treating a patient before the infection becomes sever, etc.

Figure 1:
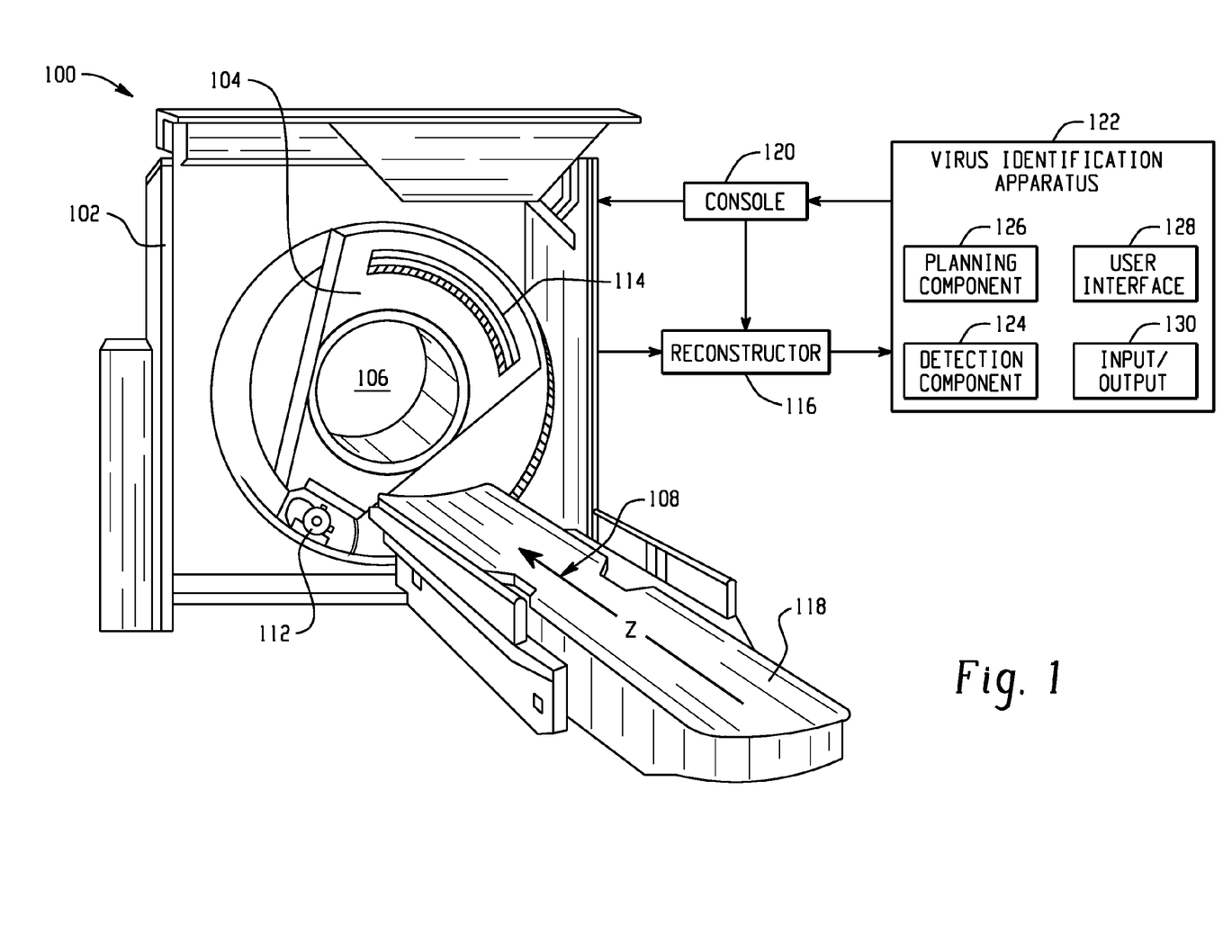
FIG. 1 illustrates an example imaging system in connection with a virus identification apparatus.

FIG. 1 illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis 108.

A radiation source 112, such as an x-ray tube, is supported by the rotating gantry 104. The radiation source 112 emits ionizing radiation from a focal spot and the radiation traverses the examination region 106 and an object or subject therein. A source collimator collimates the radiation to form a generally cone, wedge, fan or other shaped radiation beam.

A two-dimensional radiation sensitive detector array 114 subtends an angular arc opposite the radiation source 112 across the examination region 106. The detector array 114 includes a plurality of rows of detectors that extend along the z-axis direction. The detector array 114 detects radiation traversing the examination region 106 and generates projection data indicative thereof.

A reconstructor 116 reconstructs the projection data and generates three-dimensional (3D) volumetric image data indicative thereof. The volumetric image data can be processed to generate one or more images of the object or subject.

A patient support 118, such as a couch, supports an object or subject such as a human patient in the examination region 106. The patient support 118 facilitates positioning the patient along the x, y, and z-axes, before, during and/or after scanning the patient.

A general-purpose computing system or computer serves as an operator console 120. A processor of the console 120 executes computer readable instructions encoded on computer readable storage medium of the console 120, which allows the operator to control operation of the system 100 such as selecting protocols, initiating scanning, etc. The console 120 also includes input/output for receiving input and outputting information and a display for presenting information in a human readable format.

A virus identification apparatus 122 is configured to identify a virus infecting a subject. The illustrated virus identification apparatus 122 includes a detection component 124 that detects and classifies the virus. Such information can be used to detect the presence and type of an infectious disease. As described in greater detail below, in one instance the detection component 124 detects and optionally classifies the virus based on a combination of imaging data and other data.

An example of such a virus is a strain of the influenza virus (seasonal, pandemic, and/or other influenza.). By way of example, the virus identification apparatus 122 can detect and classify S-OIV, other variants of influenza, such as influenza C, and subtypes of influenza A, such as H1N1, H1N2, H3N1, H3N2, and H2N3. Other influenza A subtypes that can be detected include, but are not limited to, H2N2, H5N1, H7N7, H9N2, H7N2, H7N3, H5N2, H10N7, and/or other subtypes. Moreover, the virus identification apparatus 122 can be configured to detect non-influenza viruses.

The illustrated virus identification apparatus 122 further includes an optional planning component 126 that facilitate planning a suitable imaging exam for generating the image data used by the detection component 124. As described in greater detail below, in one instance the planning component 126 can recommend a type of imaging modality, an imaging protocol, and/or protocol parameters.

The detection component 124 further includes a user interface 128 for variously presenting information to a user. Such information includes, but is not limited to, information related to a likelihood of a patient having a particular disease, the information (imaging and non-imaging data) used to determine the likelihood, the information used to determine the imaging modality generating the imaging data, and/or other data. For example, the user interface 128 can be used to present the value indicative of the likelihood of the patient having a particular virus with the image data. In one instance, when presenting the image data, regions of the image data indicative of the virus are graphically highlighted or emphasized.

The detection component 124 further includes input/output (I/O) 130, which allows the detection component 124 to communicate with various systems. Such systems include, but are not limited to, the console 120, various data repositories (local and/or remote), electronic devices (e.g., cell phones, computers, etc.) employed by clinicians, archival databases, radiology information systems, hospital information systems, data repositories, government agencies, disease control centers, etc.

The illustrated virus identification apparatus 122 is part of a computing system that includes one or more processors that executes one or more computer readable instructions encoded in one or more computer readable storage mediums. The computing system can be part of (or integrated with) the system 100 or separate from the system 100 and located local to (as shown) or remote from the system 100. In other embodiments, one or more of the detecting component 124 or the planning component 126 can be omitted.

Figure 2:
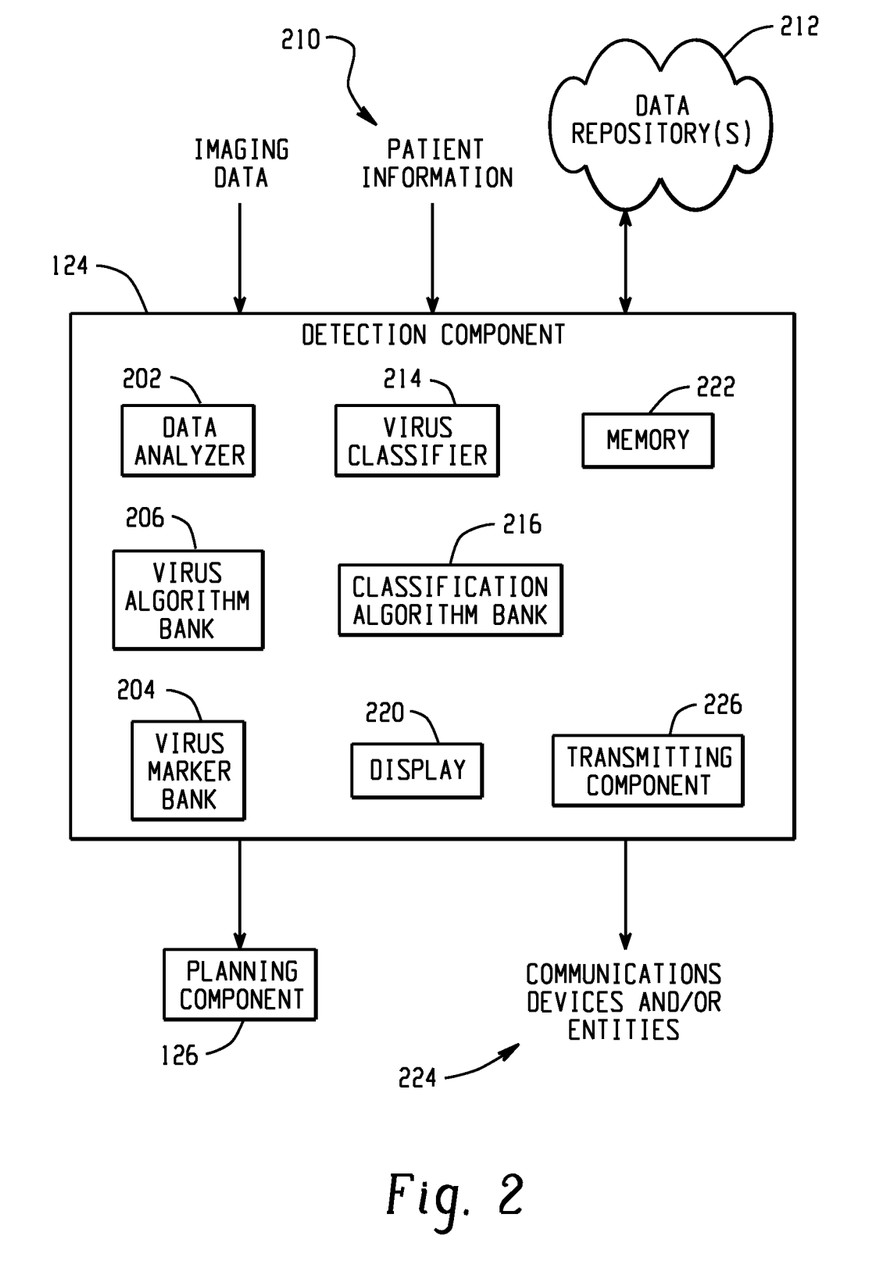
FIG. 2 illustrates an example influenza detection component of the virus identification apparatus.

FIG. 2 illustrates an example detection component 124 (of the virus identification apparatus 122 of FIG. 1).

The illustrated detection component 124 includes a data analyzer 202 that analyzes imaging data such as projection (raw) data, image data, images, and/or other imaging data. The data may be received from the imaging system 100, another system, a storage bank, etc., and may include, but is not limited to, 2D, 3D and 4D data, functional data, contrast enhanced data, low dose data, etc. The data analyzer 202 analyzes the data based on various information, such as features, markers, algorithms, patient information, and/or other information, as described in greater detail next. The detection component 124 generates a signal indicative of the analysis.

A virus marker bank 204 includes one or more sets of markers for use by the data analyzer 202. In one instance, at least one of the markers corresponds to one or more types of disease such as one or more types of influenza. For example, at least one of the sets of markers can include markers indicative of S-OIV. Examples of such markers include, but are not limited to, patchy ground-glass opacities, hilar fullness, hypoinflation of the lungs, basal and/or axial interstitial consolidation, basal and/or axial alveolar consolidation, etc. In addition to the presence of these markers, their location and distribution (e.g., predominant peribronchovascular and subpleural distribution) may also serve as markers themselves.

One or more of the sets of markers may also identify features likely to be absent and/or normal for a particular disease. For example, continuing with the above S-OIV examples, such markers may correspond to absence of mediastinal lymphadenopathy, absence of pleural or pericardial effusions, no evidence of a mosaic perfusion pattern, absence of centrolobular nodularity or tree-in-bud opacities, normal-sized bronchial airways and walls, etc.

As different strains of influenza or other viruses and image-based markers therefore are identified, the virus marker bank 204 can be updated with the newly identified markers. In addition, where an additional marker(s) is later identified for a strain already in the virus marker bank 204, the additional marker(s) can be added to the previously stored markers. In addition, a previously stored maker(s) can also be removed from the disease marker bank 204, for example, where it is determined that the marker is not reflective of the virus, is common to all viruses, etc.

A virus algorithm bank 206 includes one or more processing algorithms for use by the data analyzer 202. At least one of the algorithms corresponds to the markers in the marker bank 204. Examples of suitable algorithms includes, but are not limited to, ground-glass opacity detection/segmentation/classification, airway segmentation, automatic model-based lung/lobe segmentation, proprietary and/or other algorithms.

As noted above, the data analyzer 202 can also use patient information to analyze the imaging data. Patient information 210 includes various information such as signs and/or symptoms (e.g., fever, lethargy, lack of appetite, coughing, runny nose, sore throat, nausea, vomiting, diarrhea, congestion, difficulty breathing, sweating, etc.), vital signs (e.g., temperatures, blood pressure, heart rate, respiration rate, etc.), pain level (e.g., from 1-10), pupil size, demographics (e.g., age, gender, race, etc.), patient medical history, family medical history, findings from previous tests and/or studies (e.g., white blood cell count, red blood cell count, lumbar puncture, serum chemistry, oxygen saturation, creatinine, nasopharyngeal swab, influenza rapid antigen test (for seasonal flu), urine test, sputum test, physical examination, bipap, heart, breath and/or bowel sounds, etc.), etc.

The patient information 210 may also include information such as a city of residence, a location of the patient's employer, places frequented during the past month or so, school enrollment records, memberships, etc. This information can be used to determine a likelihood of personal contact with others, some of which who may have been infected and modulated the spread of the disease. Such information may be additionally used to form models of disease propagation and/or a pattern of spread, point source exposure type, and for identification of others who may be notified should a positive diagnosis of the current individual be made.

The data analyzer 202 can also employ various other information such as, but not limited to, imaging information, non-imaging information, signs, symptoms, diagnoses, outcomes for other patients, local, regional, national and/or international statistical analyses, disease specific information such as geographic activity, demographic distributions, severity indices, frequencies of visits to healthcare providers, hospitalization, proportion of deaths attributed to a disease, etc. Some of this information can be obtained from the patient.

Some of above information can also be obtained electronically via various data repositories 212 such as, but not limited to, hospitals, healthcare agencies, local, national and/or federal government agencies, the Centers for Disease Control and Prevention (CDC), the World Health Organization (WHO), the European Influenza Surveillance Network (EISN), the Public Health Agency of Canada, Center for Health Protection (Hong Kong), Chinese Center for Disease Control and Prevention, European Centre for Disease Prevention and Control (ECDC), Health Protection Agency (HPA) (United Kingdom), Institut de veille sanitaire (IVS) (France), Istituto Superiore di Sanita (ISS) (Italy), Robert Koch Institute (Germany), Public Health Advisor, Epidemic Intelligence Service, etc.

A virus classifier 214 classifies the virus identified in output signal of the data analyzer 202. In one instance, the classifier 214 classifies the output signal as corresponding to a particular virus from a predetermined set of viruses. For example, the virus classifier 214 may classify an influenza virus as the H1N1 virus. The classification may include indicia indicating a likelihood (e.g., from 0 to 1 (certain event)) or probability that the patient has the virus based on the signal.

In another embodiment, the classifier 214 may indicate that the signal is likely to belong to one or more of a subset of viruses from the set of viruses. In this instance, the classifier 214 can provide a likelihood for one or more of the viruses in the subset. The classifier 214 can also be configured to generate a likelihood that the patient does not have a particular virus and/or a signal indicating that it detects a virus, but cannot classify it.

In the illustrated embodiment, the classifier 214 employs various algorithms to classify the signal such as machine learning algorithms stored in a classification algorithm bank 216. In one instance, the classifier 214 is a fixed classifier that employs a fixed algorithm. In another instance, the classifier 214 is a learning classifier that dynamically updates algorithms based on test cases with known results and/or from confirmation and/or rejection of its classification results.

Examples of suitable classifiers include, but are not limited to, neural networks, support vector machines, k-nearest neighbors, Gaussian classifiers, Bayesian networks, decision trees, cost functions, radial basis functions, hidden Markov models, linear classifiers, regression classifiers, case similarity search engines, case-based reasoning systems, rule-based systems, and/or other classifiers.

The output of the classifier 214 as well as various information obtained by the detection component 124 can be presented or displayed via a display 220, stored in storage such as local memory 222, portable memory further processed, used to train the classifier 214, etc. As noted above, the type of virus and/or the likelihood of the patient having the virus can be displayed with the image data, and regions of the image data in which markers and/or features corresponding to the virus found can be emphasized and/or highlighted. The highlighting and/or emphasis can be through color maps, overlays, text, segmented data, models of the region, etc.

The output of the classifier 214 can also be conveyed outside of the detection component 124 to various communications devices and/or entities 224 and/or the data repository 212 via a transmitting component 226. The transmitting component 226 can send information related to suspected or confirmed diagnoses, images, features, and/or related clinical information back to one or more of the sources noted above (e.g., local, national, federal, international government agencies' databases, etc.), a disease control agency, the imaging system 100, individual schools or school systems, airports, train stations, healthcare facilities (e.g., hospitals), sporting events halls, concert halls, etc.

Such information can be used to track incidence, prevalence, spread, severity, etc., of a disease, warn particular populations or health or government agencies associated therewith, etc. The information can also be used to identify and prioritize geographical locations, facilitate dissemination of vaccines and/or healthcare workers, reduce the spread of disease, etc.

As shown and as discussed further below, the output of the detection component 124 may also be provided to the planning component 126.

Figure 3:
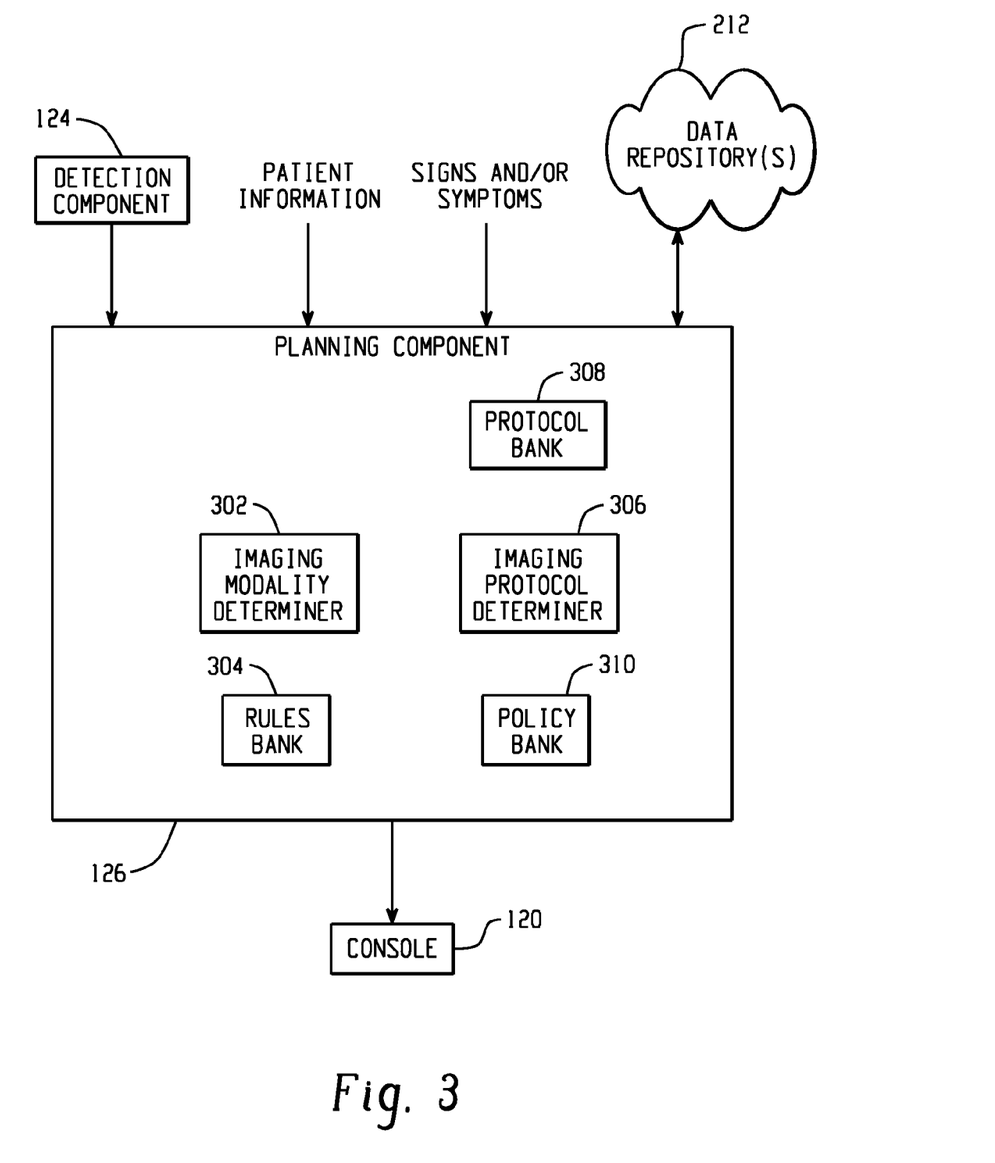
FIG. 3 illustrates an example planning component of the virus identification apparatus.

FIG. 3 illustrates an example planning component 126 (of the virus identification apparatus 122 of FIG. 1).

The illustrated planning component 126 includes an image modality determiner 302 that determines a suitable imaging modality for imaging a patient based on various input. Such input includes at least clinical signs and/or symptoms and patient information. As noted above, examples of signs and/or symptoms include, but are not limited to, fever, lethargy, lack of appetite, coughing, runny nose, sore throat, nausea, vomiting, diarrhea, congestion, difficulty breathing, sweating, etc., and examples of patient information includes age, gender, race, etc., patient medical history, family medical history, patient imaging history (e.g., lifetime dose, etc.), etc.

Other input includes one or more preliminary diagnoses and/or one or more preliminary ruled out diagnoses, data from the data repositories 212, a previous scan of the patient, risk of the imaging modality relative to patient demographics, availability of the imaging modality, access to the imaging modality, cost of the imaging procedure, a likelihood that that patient has the virus, etc.

In instances where the patient has already been imaged based on at least signs and/or symptoms, the imaging data therefrom can also be used as an input to determine whether a subsequent scan of the patient using the same and/or a different imaging modality is recommended. In instances in which the detection component 124 has determined a likelihood or probability of a virus, this information (from the detection component 124) can also be used as an input to determine whether a subsequent scan of the patient using the same and/or a different imaging modality is recommended.

Based at least on the above information, the image modality determiner 302 identifies one or more imaging modalities for imaging the patient. Suitable imaging modalities include, but are not limited to, computed tomography (CT), x-ray radiography, magnetic resonance imaging (MRI), positron emission tomography (PET), single photon emission computed tomography (SPECT), ultrasound (US), and/or other imaging such as microwave, infrared, radio wave, sonic, etc. In the context of the S-OIV example discussed herein, the above systems can be used to image structural changes, radiodensity changes, localize inflammation, determine tissue elasticity, etc. One or more of the above imaging techniques can also be used to supplement or augment findings from another imaging modality and/or non-imaging study.

In the illustrated embodiment, the image modality determiner 302 employs rules from a rules bank 304 to facilitate identifying a suitable imaging modality for the patient. By way of example, one rule for S-OIV may indicate that for a child with mild symptoms that a chest x-ray is recommended for the patient. Another rule for S-OIV may indicate that for a person with more severe symptoms that a low dose or conventional chest CT is recommended for the patient. Another rule may take into account that a disease may preferentially affect a particular population and thus balance sufficient image quality for detection with radiation dose reduction.

One or more of these rules may also recommend non-imaging based tests. Another rule may recommend not imaging patient. Other rules are also contemplated herein. The rules in the rules bank 304 may be variously generated. For example, in one instance at least one of the rules is generated based on previous patient studies, the literature, academic research, disease control agencies, clinician experience, and/or otherwise. A rule in the rule bank 304 can also be modified to incorporate the latest finding and/or removed from the rule bank 304.

An imaging protocol determiner 306 determines a suitable protocol and protocol parameters based on the recommended imaging modality and various information. In once instance, the information includes one or more protocol parameter policies 310 such as a radiation dose policy, a contrast agent policy, and/or other policy stored in a policy bank 308 or other storage. Such a policy may facilitate populating a scan protocol with suitable scan parameters for the patient based on various dose, contrast agent, and/or other predetermined criteria.

In one instance, this includes replacing and/or suggesting/recommending replacement parameters for at least one parameter of a protocol that does not satisfy a predetermined scan parameter policy for the patient with a scan parameter that satisfies the policy. An example of a policy and employing a policy is described in patent application Ser. No. 61/253,880, filed on Oct. 22, 2009, and entitled "Scan Parameter Policy," which is incorporated in its entirety herein by reference.

Once the planning component 126 determines the imaging modality and the imaging protocol, the planning component 126 outputs a signal indicative thereof. In the illustrated embodiment, the signal is provided to the console 120 of the imaging system 100 and is used to scan the patient. In other embodiments, the signal is provided to one or more other imaging systems, presented on a display so that a clinician can view, accept, confirm, reject, change, etc. the recommendation, etc. It is to be appreciated that in one instance the signal may be indicative of a single scan with a single imaging modality. In another instance, the signal is indicative of a series of scans with a single imaging modality or with multiple different imaging systems.

Figure 4:
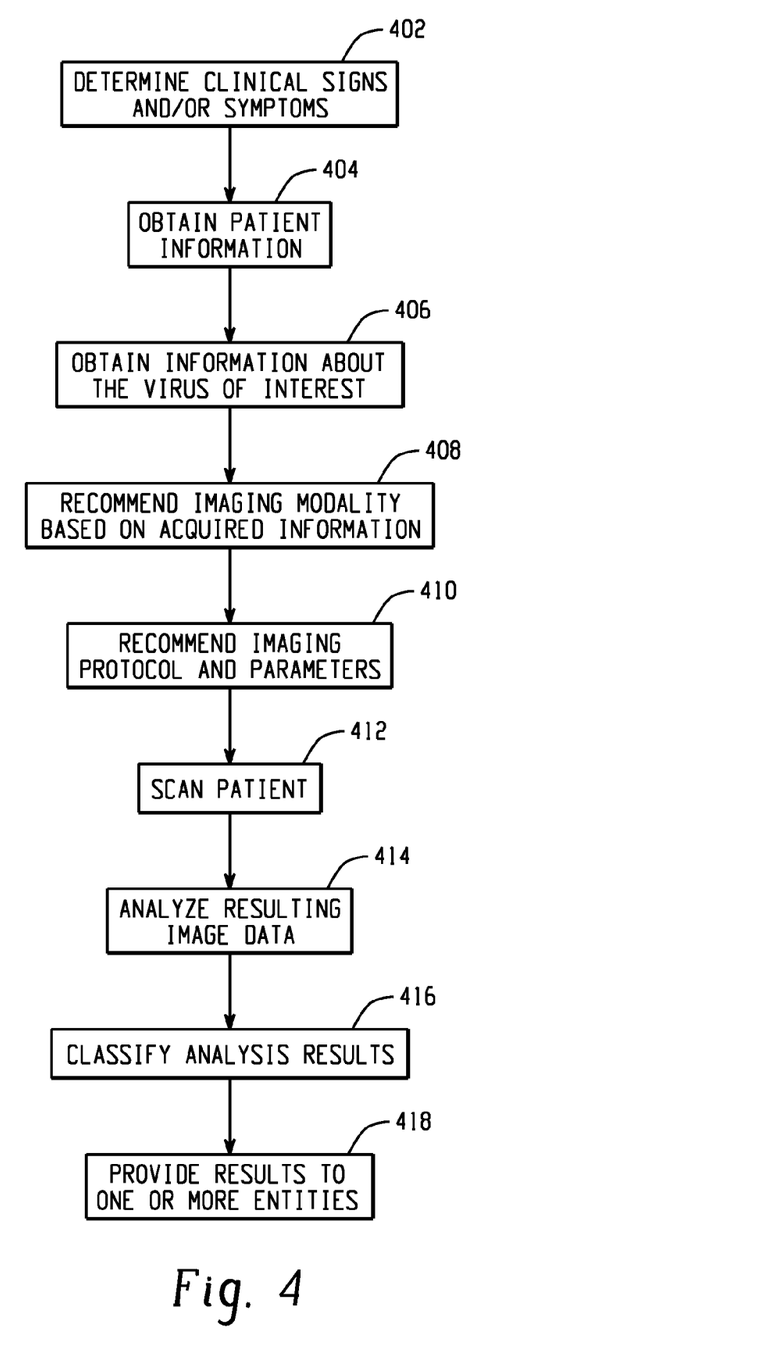
FIG. 4 illustrates a method for identifying a likelihood of influenza infection using the virus identification apparatus.

FIG. 4 illustrates a method for detecting and determining a likelihood that a patient has a particular virus such as S-OIV. It is also to be appreciated that the acts described are for explanatory purposes and not limiting. For example, another suitable method may include more or less acts, including different acts. In addition, one or more acts of one or more of the methods may occur in a different order that listed.

At 402, clinical signs and/or symptoms are determined for a patient. The signs and/or symptoms can be variously determined. For example, the patient can be asked various questions like how much pain they are in, what hurts, how long have they felt this way, etc. Other information such as temperature, blood oxygen saturation, ECG, etc. can be determined using an appropriate medical instrument or device. Still other information such as the coloring of the patient, pupil dilation, rate or amount of perspiration, etc, can be observed or captured via a video or image recording device (e.g., a camcorder, a camera, etc.). Still other information can be retrieved from a database.

At 404, patient information such as medical history, family medical history, demographics, etc. can be obtained. Such information can be retrieved from an electronic database, the patient, and/or other source. In another instance, act 404 is omitted.

At 406, various virus related information from sources such as government agencies, disease control entities, hospitals, etc. can also be obtained. In another instance, act 406 is omitted.

At 408, the signs, the symptoms, the patient information, the virus information, and/or other information are used to identify and recommend a suitable medical procedure for the patient. For example, this information can be used to determine whether the patient should be scanned and the type of scan such as an x-ray system, a CT scanner, or other medical imaging system.

At 410, where it is determined that the patient should be scanned, a protocol and protocol parameters are determined and recommended for the selected imaging modality(s). The protocol and parameters can be selected based on various information as discussed herein, including, but not limited to, the signs, the symptoms, the patient information, the disease information, an imaging policy, and/or other information.

Acts 408 and/or 410 can additionally or alternatively be implemented with interaction via a clinician or other authorized personnel.

At 412, the patient is scanned using the recommended protocol and parameters. Of course, the clinician can use a different imaging modality, protocol, and/or protocol parameters.

At 414, the imaging data is analyzed for viruses of interest based on various information using corresponding algorithms as discussed herein. Such information includes, but is not limited to, predetermined features and/or markers correlated with viruses, the signs and/or symptoms, the patient information, the virus information from the various sources, and/or other information. The analysis includes generating a signal indicative of the results.

At 416, the results of the analysis are classified. Such classification may include employing machine learning or other techniques for determining a likelihood(s) that a patient has one or more particular viruses based on the results of the analysis.

At 418, the results (e.g., the output of the analysis, the likelihood, etc.) are provided to one or more entities such as government agencies, virus control centers, etc. as discussed herein. Other information including, but not limited to, the image data, input used by the detection component 124, and/ or other information can concurrently or serially provided with the results. In addition, such information can also be stored in local and/or remote memory, presented via a display, conveyed to another device (e.g., a computer, a cell phone, a monitoring station, etc.), further processed, etc.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method for detecting a virus in a patient based at least on imaging data, comprising:
    scanning a region of interest of the patient with an imaging device and generating imaging data indicative of the region of interest;
    identifying, via a processor, at least one marker in the image data that corresponds to the virus based on a set of predetermined imageable markers that correspond to the virus;
    classifying, via the processor, the virus as a particular strain of the virus based on the at least one identified marker and a set of classification rules;
    generating a signal indicative of the particular strain;
    wherein the virus is an influenza virus.

2. The method of claim 1, wherein the virus is a strain of a swine-origin influenza virus.

3. The method of claim 1, further comprising:
    electronically conveying the signal to at least one of a government agency, a disease control agency, healthcare facilities, a school, a school systems, an airport, a train station, a sporting event facility, a concert hall, and the imaging device.

4. The method of claim 3, wherein the signal facilitates prioritizing dissemination of at least one of vaccines or healthcare workers amongst geographical locations.

5. The method of claim 3, wherein the signal facilitates modelling at least one of a virus propagation pattern, a source region of the virus, or identification of a population to notify regarding the classification.

6. The method of claim 1, further comprising:
    generating a likelihood or probability that the virus is the particular strain.

7. The method of claim 1, wherein the set of predetermined markers includes at least one maker whose presence in the image data indicates a virus infection.

8. The method of claim 7, wherein the set of predetermined markers includes at least one of patchy ground-glass opacities, hilar fullness, hypoinflation of the lungs, basal interstitial consolidation, axial interstitial consolidation, basal alveolar consolidation, or axial alveolar consolidation.

9. The method of claim 1, wherein the set of predetermined markers include at least one maker whose absence from or normalcy in the image data indicates a virus infection.

10. The method of claim 9, wherein the set of predetermined markers includes at least one of an absence of mediastinal lymphadenopathy, pleural effusion, pericardial effusion, mosaic perfusion pattern, centrolobular nodularity, tree-in-bud opacities, normal-sized bronchial airways, or normal-sized bronchial bronchial walls.

11. The method of claim 1, wherein the act of identifying further includes identifying the at least one marker based on one or more of patient demographics, findings from other tests, severity indices, frequencies of visits to healthcare providers, hospitalization, proportion of deaths attributed to the virus disease, or information from health information data repositories.

12. The method of claim 1, further comprising:
    presenting the signal concurrently with the image data.

13. The method of claim 12, further comprising:
    graphically highlighting one or more regions of the image data corresponding to the identified markers.

14. The method of claim 1, further comprising:
    determining, via the processor, that the patient is likely to have the virus based at least in part on symptoms of the patient;
    identifying, via the processor, an imaging modality to scan the patient based at least in part on patient demographics; and
    scanning the chest region of the patient employing the identified imaging modality.

15. The method of claim 14, further comprising:
    identifying that imaging modality based at least in part on one or more of a patient medical history, a family medical history, or an imaging protocol policy.

16. A system, comprising:
    a virus detection apparatus that detects a virus in a patient based on imaging data, the virus detection apparatus, including:
        a data analyzer with a processor that analyzes the image data and identifies at least one feature in the image data that corresponds to the virus based on a set of predetermined features that correspond to the virus;
        a virus classifier with a processor that classifies the virus as a particular strain of the identified virus based on the feature and generates a signal indicative of the particular strain;
        wherein the virus is an influenza virus.

17. The system of claim 16, wherein the virus a strain of a swine-origin influenza virus.

18. The system of claim 16, further comprising:
    a transmitting component that electronically transmits the signal to at least one recipient located remote from the system.

19. The system of claim 16, further comprising:
    a classification algorithm bank that includes a set of classification algorithms that map the identified at least one feature to a virus type, and wherein the virus classifier classifies the virus as a particular type of the virus based at least in part on the set of classification algorithms.

20. The system of claim 16, wherein the set of predetermined features includes one or more of a first feature whose presence in the image data indicates an influenza virus infection or a second feature whose absence or normalcy in the image data indicates an influenza virus infection.

21. The system of claim 16, further comprising:
    an imaging modality determiner that identifies an imaging modality for scanning the patient based at least in part patient symptoms, wherein the imaging data analyzed by the data analyzer is generated by the identified imaging modality.

22. The system of claim 21, wherein the imaging modality determiner identifies the imaging modality based on one or more of patient demographics, a previous scan of the patient, risk of the imaging modality relative to patient demographics, availability of the imaging modality, access to the imaging modality, cost of the imaging procedure, or a likelihood that that patient has the virus.

23. A non-transitory computer readable storage medium containing instructions which, when executed by a computer, cause the computer to perform the acts of:
- scanning a region of interest of a patient and generating imaging data indicative of the region of interest with an imaging device;
- detecting a presence of a virus infection in the patient based on the imaging data;
- classifying the infection as a particular strain of the virus;
- wherein the virus is an influenza virus.

24. The non-transitory computer readable storage medium of claim 23, further containing instructions which, when executed by the computer, cause the computer to perform the acts of:
- generating a signal indicative of the classification; and
- electronically conveying the signal to at least one entity remote from the computer.

* * * * *